US010815164B2

(12) United States Patent
Van Mourik

(10) Patent No.: US 10,815,164 B2
(45) Date of Patent: Oct. 27, 2020

(54) PROCESS FOR PRODUCING STYRENE

(71) Applicant: SHELL OIL COMPANY, Houston, TX (US)

(72) Inventor: Arian Van Mourik, Amsterdam (NL)

(73) Assignee: Shell Oil Company, Houston, TX (US)

( * ) Notice: Subject to any disclaimer, the term of this patent is extended or adjusted under 35 U.S.C. 154(b) by 1 day.

(21) Appl. No.: 15/767,711

(22) PCT Filed: Oct. 17, 2016

(86) PCT No.: PCT/EP2016/074892
§ 371 (c)(1),
(2) Date: Apr. 12, 2018

(87) PCT Pub. No.: WO2017/067887
PCT Pub. Date: Apr. 27, 2017

(65) Prior Publication Data
US 2018/0297910 A1    Oct. 18, 2018

(30) Foreign Application Priority Data
Oct. 19, 2015    (EP) .................................... 15190427

(51) Int. Cl.
*C07C 1/24*    (2006.01)
*C07C 7/05*    (2006.01)
(Continued)

(52) U.S. Cl.
CPC ................ *C07C 1/24* (2013.01); *C07C 7/005* (2013.01); *C07C 7/05* (2013.01); *C07C 7/10* (2013.01); *C07C 15/46* (2013.01); *C07C 2521/04* (2013.01)

(58) Field of Classification Search
CPC ....................................................... B01D 3/38
See application file for complete search history.

(56) References Cited

U.S. PATENT DOCUMENTS 3,515,766 A * 6/1970 Root ....................... C07C 5/321
                                                              210/663
3,943,160 A    3/1976 Farmer, III et al.
(Continued)

FOREIGN PATENT DOCUMENTS

CN        101743300 A     6/2010
EP          0377261 A2     7/1990
(Continued)

OTHER PUBLICATIONS

International Search Report and Written Opinion received for PCT Patent Application No. PCT/EP2012/059891, dated Sep. 20, 2012, 11 pages.
(Continued)

*Primary Examiner* — In Suk C Bullock
*Assistant Examiner* — Alyssa L Cepluch

(57) ABSTRACT

The invention relates to a process for the preparation of styrene or substituted styrenes comprising the steps of:
(a) subjecting a feed containing 1-phenyl ethanol or substituted 1-phenyl ethanol to a dehydration treatment in the presence of a suitable dehydration catalyst;
(b) subjecting the resulting product mixture to a separation treatment, thus obtaining a stream containing water and styrene or substituted styrene and a residual fraction containing heavy ends;
(c) treating the stream containing water and styrene or substituted styrene with a base;
(d) separating the treated stream of step (c) into a styrene or substituted styrene-rich product stream and a styrene or substituted styrene-lean waste water stream;
(e) treating the styrene or substituted styrene-lean waste water stream with steam in a stripping column, thus
(Continued)

obtaining a treated waste water stream and a treated stream comprising steam and styrene or substituted styrene.

9 Claims, 1 Drawing Sheet

(51) Int. Cl.
  *C07C 7/10* (2006.01)
  *C07C 7/00* (2006.01)
  *C07C 15/46* (2006.01)

(56) References Cited

U.S. PATENT DOCUMENTS

| | | |
|---|---|---|
| 3,946,812 A | 3/1976 | Gale et al. |
| 4,029,608 A | 6/1977 | Murata et al. |
| 4,077,471 A | 3/1978 | Shupe et al. |
| 4,183,867 A | 1/1980 | Kitano et al. |
| 4,216,079 A | 8/1980 | Newcombe |
| 4,248,793 A | 2/1981 | Sekiguchi et al. |
| 4,597,879 A | 7/1986 | Morita et al. |
| 4,822,501 A | 4/1989 | Debons et al. |
| 4,979,564 A | 12/1990 | Kalpakci et al. |
| 5,068,043 A | 11/1991 | Thigpen et al. |
| 5,076,363 A | 12/1991 | Kalpakci et al. |
| 5,103,909 A | 4/1992 | Morgenthaler et al. |
| 5,108,646 A | 4/1992 | Beerse et al. |
| 5,114,599 A | 5/1992 | Debons et al. |
| 5,199,490 A | 4/1993 | Surles et al. |
| 5,284,206 A | 2/1994 | Surles et al. |
| 5,318,709 A | 6/1994 | Wuest et al. |
| 5,510,306 A | 4/1996 | Murray |
| 5,633,422 A | 5/1997 | Murray |
| 5,648,584 A | 7/1997 | Murray |
| 5,648,585 A | 7/1997 | Murray |
| 5,654,261 A | 8/1997 | Smith |
| 5,723,423 A | 3/1998 | Van Slyke |
| 5,849,960 A | 12/1998 | Singleton et al. |
| 6,022,834 A | 2/2000 | Hsu et al. |
| 6,100,439 A * | 8/2000 | Hart ............ C07C 7/10 585/806 |
| 6,269,881 B1 | 8/2001 | Chou et al. |
| 6,420,620 B1 * | 7/2002 | De Bie ............ C07C 1/20 585/319 |
| 6,427,268 B1 | 8/2002 | Davis |
| 6,439,308 B1 | 8/2002 | Wang |
| 2008/0300416 A1 | 12/2008 | Nisbet et al. |
| 2009/0163669 A1 | 6/2009 | Sinquin et al. |
| 2010/0282467 A1 | 11/2010 | Hutchison et al. |
| 2010/0324325 A1 | 12/2010 | Goda et al. |
| 2011/0000987 A1 | 1/2011 | Fujioka et al. |
| 2011/0166374 A1 | 7/2011 | Fujioka et al. |

FOREIGN PATENT DOCUMENTS

| | | |
|---|---|---|
| EP | 0482687 A1 | 4/1992 |
| EP | 0351928 B1 | 6/1993 |
| EP | 2169043 A1 | 3/2010 |
| EP | 2261298 A1 | 12/2010 |
| RU | 2006123456 A | 1/2008 |
| WO | 9640587 A1 | 12/1996 |
| WO | 2004081342 A2 | 9/2004 |
| WO | 2006029676 A1 | 3/2006 |

OTHER PUBLICATIONS

Barnes et al., "Application of Internal Olefin Sulfonates and Other Surfactants to EOR, Part 1: Structure-Performance Relationships for Selection at Different Reservoir Conditions", SPE Improved Oil Recovery Symposium, Apr. 24-28, 2010, XP055009775.

Levitt et al., "Identification and evaluation of high-performance EOR surfactants", SPE International Oil and Gas Conference and Exhibition, SPE Reservoir Evaluation & Engineering, 2006, vol. 12, issue No. 2, pp. 1-11.

Showell, "Powdered Detergents", Surfactant Science Series, 1998, vol. 71, chapter 2, Compact Powdered Detergent Process Technologies, pp. 21-42.

Chatzis, "Correlation of Capillary Number Relationship for Sandstone", 1989, SPE Journal, vol. 29, pp. 555-562.

Falls et al., "Field Test of Cosurfactant-Enhanced Alkaline Flooding", Society of Petroleum Engineers, Reservoir Engineering, 1994.

Liu et al., "Favorable Attributes of Alkaline Surfactant-Polymer Flooding", SPE Journal, Mar. 2008, pp. 5-16.

Rashidi et al., "Viscosity Study of Salt Tolerant Polymers," Journal of Applied Polymer Science, 2010, vol. 117, pp. 1551-1557.

Adami, "Production of Linear Alkylbenzene Sulphonate and Alpha-Olefin Sulphonates", Surfactant Science Series, vol. 142, chapter 5, p. 83.

Wellington et al., "Low Surfactant Concentration Enhanced Waterflooding", SPE Annual Technical Conference and Exhibition, Oct. 22-25, 1995, 17 pages.

Van Os et al., "Anionic Surfactants: Organic Chemistry", Surfactant Science Series 56, 1996, Chapter 7: Olefin Sulfonates, p. 363.

International Search Report and Written Opinion received for PCT Patent Application No. PCT/EP2016/074892, dated Jan. 16, 2017, 9 Pages.

Buijink et al., Propylene Epoxidation via Shell's SMPO Process, Mechanisms in Homogeneous and Heterogeneous Epoxidation Catalysis, Elsevier, Dec. 2008, pp. 367-369.

Buijink et al., Propylene Epoxidation via Shell's SMPO Process, Mechanisms in Homogeneous and Heterogeneous Epoxidation Catalysis, Elsevier, Dec. 2008, pp. 358-362.

\* cited by examiner

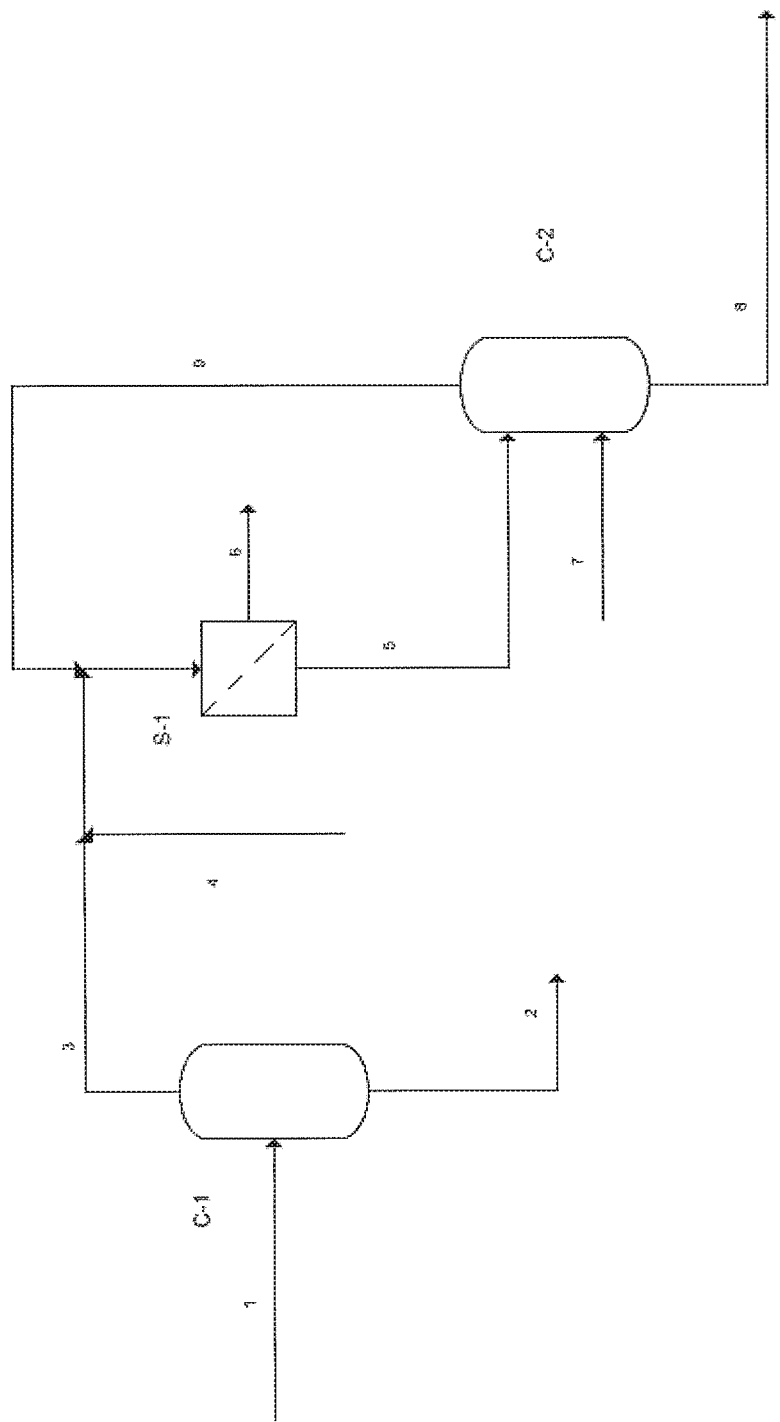

PROCESS FOR PRODUCING STYRENE

CROSS REFERENCE TO RELATED APPLICATIONS

This is a national stage application of International application No. PCT/EP2016/074892, filed 17 Oct. 2016, which claims benefit of priority of European application No. 15190427.3, filed 19 Oct. 2015.

FIELD OF THE INVENTION

The present invention relates to a process for producing styrene.

BACKGROUND OF THE INVENTION

Processes for the joint preparation of styrene and propylene oxide are well known in the art and are commonly referred to as styrene monomer/propylene oxide (SM/PO) processes.

In general, a SM/PO process comprises the steps of:
(a) reacting ethene and benzene to form ethylbenzene,
(b) reacting ethylbenzene with oxygen or air to form ethylbenzene hydroperoxide,
(c) reacting at least part of the ethylbenzene hydroperoxide obtained with propylene in the presence of an epoxidation catalyst to form propylene oxide and 1-phenyl ethanol (also known as methylphenyl carbinol (MPC)), and
(d) dehydrating at least part of the 1-phenyl ethanol obtained into styrene in the presence of a suitable dehydration catalyst.

Step (a) above may be performed as an integral part of an SM/PO process or, alternatively, may be performed as a separate step, for example at another location, prior to step (b).

Thus, in said SM/PO process, styrene is produced via ethylbenzene hydroperoxide which is used to convert propylene into propylene oxide thereby also forming 1-phenyl ethanol, as follows:

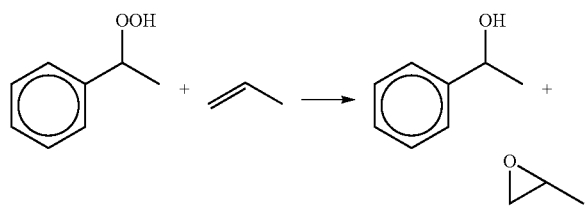

In a next step, said 1-phenyl ethanol is converted into styrene by dehydration, as follows:

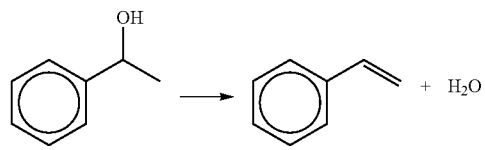

A disadvantage of the production of styrene via the above-mentioned SM/PO process is that during purification and work-up of product streams, styrene has to be separated from water and is therefore present in waste water streams and can polymerise and cause fouling in heat exchangers present in waste water treatment plants which use thermal processes.

Such fouling necessitates regular cleaning of heat exchange equipment in waste water plants which is not only costly, but also time consuming.

Therefore, it is desired to provide a process for producing styrene which maximises the yields of styrene recovered from various product and waste streams whilst also reducing the amount of heat exchanger fouling.

SUMMARY OF THE INVENTION

Surprisingly, in the present invention there has been found a process for the production of styrene from 1-phenyl ethanol which not only allows for greater recovery of styrene from waste water streams, but which also reduces the amount of heat exchanger fouling.

Accordingly, the present invention relates to a process for the preparation of styrene or substituted styrenes comprising the steps of:
(a) subjecting a feed containing 1-phenyl ethanol or substituted 1-phenyl ethanol to a dehydration treatment in the presence of a suitable dehydration catalyst;
(b) subjecting the resulting product mixture to a separation treatment, thus obtaining a stream containing water and styrene or substituted styrene and a residual fraction containing heavy ends;
(c) treating the stream containing water and styrene or substituted styrene with a base;
(d) separating the treated stream of step (c) into a styrene or substituted styrene-rich product stream and a styrene or substituted styrene-lean waste water stream;
(e) treating the styrene or substituted styrene-lean waste water stream with steam in a stripping column, thus obtaining a treated waste water stream and a treated stream comprising steam and styrene or substituted styrene.

BRIEF DESCRIPTION OF THE DRAWING

The FIGURE is a diagram showing an embodiment of the present styrene production process wherein there is an integration with the above-mentioned SM/PO process.

DETAILED DESCRIPTION OF THE INVENTION

The production of styrene and substituted styrenes by dehydrating 1-phenyl ethanol and substituted 1-phenyl ethanol is well known in the art and can be carried out both in the gas phase and in the liquid phase.

Suitable dehydration catalysts include, for instance, acidic materials such as alumina, alkali alumina, aluminium silicates and H-type synthetic zeolites.

Dehydration conditions are also well known and usually include reaction temperatures in the range of from 100 to 200° C. for liquid phase dehydration and in the range of from 210 to 320° C., typically in the range of from 280 to 310° C., for gas phase dehydration. Pressures usually range from 0.1 to 10 bar.

In principle any known dehydration process can be applied in step (a) of the process according to the present invention. For the purpose of the present invention, gas phase dehydration is preferred.

In a preferred embodiment, the gas phase dehydration is carried out at a temperature in the range of 230 to 320° C., more preferably in the range of from 260 to 320° C., using an alumina-based dehydration catalyst. It has been found advantageous to apply these relatively low temperatures for gas phase dehydration so as to limit the formation of high boiling components like polystyrenes. The latter will add to the heavy ends from which no valuable products can be obtained.

Suitable conditions for effecting the conversion in step (a) are disclosed by J. K. F. Buijink et al. in Section 3.3 ("Catalytic dehydration") from Chapter 13 ("Propylene Epoxidation via Shell's SMPO Process: 30 Years of Research and Operation") from "Mechanisms in Homogeneous and Heterogeneous Epoxidation Catalysis", edited by T. Oyama, Elsevier, 2008, pages 367-369, the entire disclosure of which is herein incorporated by reference.

The feed containing 1-phenyl ethanol or substituted 1-phenyl ethanol used in step (a) of the present process is suitably obtained from a preceding epoxidation step, wherein optionally substituted ethylbenzene hydroperoxide is reacted with propene to yield propylene oxide and 1-phenyl ethanol or substituted 1-phenyl ethanol.

In such an epoxidation step, a homogeneous catalyst or a heterogeneous catalyst can be applied. As homogeneous catalysts molybdenum compounds are frequently applied, while catalysts based on titanium on a silica carrier are often used as heterogeneous catalysts. Conditions under which epoxidation is carried out are well known in the art and include temperatures of 75 to 150° C. and pressures up to 80 bar with the reaction medium being in the liquid phase.

For example, conversion of ethylbenzene hydroperoxide (EBHP) and propylene into propylene oxide, 1-phenyl ethanol and methylphenyl ketone (MPK) may be carried out in the liquid phase at a temperature of from 30 to 200° C., preferably 50 to 150° C. and at a pressure of from 10 to 100 bar (1 to 10 MPa), preferably 30 to 70 bar (3 to 7 MPa). Propylene may be used in excess. The molar ratio of propylene to EBHP may be of from 2 to 10, typically 3 to 8. Further, preferably, the catalyst is a titanium containing catalyst, which is preferably supported on silica. The latter catalyst may be prepared in a multistep gas-phase process by treatment of a silica carrier with titanium tetrachloride, heating the obtained material, followed by steaming and silylation. Suitable conditions for effecting said conversion are disclosed by J. K. F. Buijink et al. in Section 2 ("Catalytic Epoxidation") from Chapter 13 ("Propylene Epoxidation via Shell's SMPO Process: 30 Years of Research and Operation") from "Mechanisms in Homogeneous and Heterogeneous Epoxidation Catalysis", edited by T. Oyama, Elsevier, 2008, pages 358-362, the entire disclosure of which is herein incorporated by reference.

The effluent from the epoxidation step is normally first subjected to a separation treatment to remove the propylene oxide formed, after which the residual stream, containing 1-phenyl ethanol, is suitably subjected to one or more further separation treatments, inter alia to remove ethylbenzene for reuse in an earlier stage of the process.

Step (b) of the process of the present invention comprises subjecting the resulting product mixture from step (a), and which inter alia contains the styrene monomer formed, to a separation treatment. The styrene-rich fraction, that is to say, the stream containing styrene or substituted styrene, which also contains the dehydration water, will be removed as the top fraction, whilst a residual fraction containing heavy ends formed during the dehydration will be obtained as the bottom fraction. Such separation can be effected in several ways, but most suitably is achieved by flashing or distillation.

The separated top fraction from step (b), that is to say, the stream containing water and styrene or substituted styrene also contains acids.

Consequently, in step (c), the stream containing water and styrene or substituted styrene undergoes treatment with base in order to neutralize any acids present in the stream. Suitable base materials are not limited and may be typically selected from one or more of sodium hydroxide, potassium hydroxide, sodium carbonate and potassium carbonate.

Upon treatment in step (c), the stream containing water and styrene or substituted styrene also contains the neutralized acids and a small amount of excess base, such that the pH is typically between 7 and 10, preferably between 8 and 9.

The treated stream of step (c) is then separated in step (d) into a styrene or substituted styrene-rich product stream and a styrene or substituted styrene-lean waste stream by mechanical means via settling, coalescing or centrifuging, preferably via simple settling and coalescing. This separation is performed at the same temperature, that is achieved upon condensation of the crude product stream at 40 to 90° C., preferably between 45 and 65° C.

Optionally, a portion of the styrene or substituted styrene-rich product stream from step (d) may be recycled to step (a) of the process, i.e. to the separation unit, in order to act as refluxing agent.

In step (e) of the process of the present invention, the styrene or substituted styrene-lean waste water stream from step (d) is treated with steam in a stripping column, thus obtaining a treated waste water stream and a treated stream comprising steam and styrene or substituted styrene.

Steam may be obtained from re-boiled bottom product of the stripping column or by injected as "live steam" from an external source. The stripping column may operate at atmospheric pressure, above atmospheric pressure or under vacuum in order to minimize styrene polymerization in the column. Preferably, the pressure is between 0.3 and 0.8 bara (0.03 to 0.08 MPa).

Optionally, some or all of the treated stream comprising steam and styrene or substituted styrene from step (e) may be recycled to step (d) of the process. Said stream may optionally undergo further treatment prior to being recycled to step (d).

As mentioned above, the present styrene production process may be conveniently integrated with a SM/PO process.

For example, with reference to the FIGURE, in a first epoxidation section (not shown in the FIGURE), ethylbenzene hydroperoxide and propylene are sent to an epoxidation reaction unit wherein they are converted into a product mixture comprising propylene oxide, 1-phenyl ethanol and methylphenyl ketone (MPK). Said mixture comprising propylene oxide, 1-phenyl ethanol and methylphenyl ketone may also comprise unconverted propylene which may be separated from said mixture and recyled to the epoxidation reaction unit (not shown in the FIGURE). Said product mixture comprising propylene oxide, 1-phenyl ethanol and methylphenyl ketone is sent to a separation unit (not shown in the FIGURE) wherein propylene oxide is separated from heavier components, including 1-phenyl ethanol and methyl phenyl ketone, which fraction is further subject to separation, resulting in a mixture comprising 1-phenyl ethanol and methylphenyl ketone.

Said mixture comprising 1-phenyl ethanol and methylphenyl ketone is sent via a line to a dehydration reactor (not shown in the FIGURE) wherein it is converted in the presence of a dehydration catalyst into a mixture 1 comprising styrene and methylphenyl ketone. Said mixture 1 comprising styrene and methylphenyl ketone may also comprise water which may be optionally separated from said mixture (not shown in the FIGURE).

The mixture 1 comprising styrene and methylphenyl ketone is sent to separation unit C-1 wherein styrene and water in said mixture are separated via line 3 from the residual fraction containing heavy ends and methylphenyl ketone therein, which leaves via line 2.

The mixture of heavy ends and methylphenyl ketone from line 2 may be further separated to yield methylphenyl ketone, which is recycled, and heavy ends which leave the process as a fuel.

Thereafter, the stream 3 containing water and styrene or substituted styrene is treated with a base 4 and separated in a decanting vessel S-1. The treated stream is separated into a styrene or substituted styrene-lean waste water stream 5 and a styrene or substituted styrene-rich product stream 6. The crude styrene or substituted styrene-rich product stream 6 may undergo further purification (not shown in the FIGURE). The styrene or substituted styrene-lean waste water stream 5 is stripped with steam introduced via line 7 in a stripping column C-2, thus obtaining a treated waste water stream 8, essentially free of styrene and a treated stream 9 comprising steam and styrene or substituted styrene.

Optionally, the treated stream 9 comprising steam and styrene or substituted styrene may be recycled to S-1 or C-1 for further recovery of styrene or substituted styrene therefrom via line 6.

Furthermore, the treated waste water stream 8 may contain a variety of non-stripped organic components, such as organic salts. Optionally, said stream may be further purified to enable discharge into the environment. Such purification processes may include, but are not limited to, biotreatment, treatment with oxidizers, adsorption and incineration.

Examples

The Example was obtained by computer simulation (using Aspen modelling software) of the reactor set-up shown in the FIGURE.

Table 1 shows the results of simulating the stripping process of C-2 using a "live steam" stripping column.

Said simulation provides the following information on key components of the compositions of the streams going into and exiting the column per the designated streams in the FIGURE.

TABLE 1

|  | Feed water stream 5 | Stripping steam stream 7 | Stream 9 | Stripped water stream 8 |
| --- | --- | --- | --- | --- |
| Phase | LIQUID | VAPOR | VAPOR | LIQUID |
| Total Flow, kg/hr | 19350 | 1500 | 543 | 20306 |
| Temperature, deg C. | 61 | 130 | 86 | 90 |
| Pressure, kPa | 1030 | 250 | 60 | 70 |
| Composition, ppm | | | | |
| Ethylbenzene (EB) | 2 | 0 | 82 | 0 |
| Styrene (SM) | 519 | 0 | 18470 | 0.001 |
| Methylphenyl ketone (MPK) | 70 | 0 | 1615 | 24 |

TABLE 1-continued

|  | Feed water stream 5 | Stripping steam stream 7 | Stream 9 | Stripped water stream 8 |
| --- | --- | --- | --- | --- |
| 1-phenyl ethanol | 61 | 0 | 241 | 52 |
| $H_2O$ (wt. %) | 100 | 100 | 98 | 100 |

Feed water stream 5 in Table 1 contains 519 ppm of styrene. In contrast, it is apparent from Table 1 that after application of step (e) of the process of the present invention, the stripped water stream 8 is essentially free from styrene.

That which is claimed is:

1. A process for the preparation of styrene or substituted styrenes comprising the steps of:
   (a) subjecting a feed containing 1-phenyl ethanol or substituted 1-phenyl ethanol to a dehydration treatment in the presence of a suitable dehydration catalyst;
   (b) subjecting the resulting product mixture to a separation treatment, thus obtaining a stream containing water and styrene or substituted styrene and a residual fraction containing heavy ends;
   (c) treating the stream containing water and styrene or substituted styrene with a base;
   (d) separating the treated stream of step (c) into a styrene or substituted styrene-rich product stream and a styrene or substituted styrene-lean waste water stream;
   (e) treating the styrene or substituted styrene-lean waste water stream with steam in a stripping column, thus obtaining a treated waste water stream and a treated stream comprising steam and styrene or substituted styrene.

2. The process according to claim 1, wherein the 1-phenyl ethanol or substituted 1-phenyl ethanol used in step (a) is obtained from a preceding epoxidation step, wherein optionally substituted ethylbenzene hydroperoxide is reacted with propylene to yield propylene oxide and 1-phenyl ethanol or substituted 1-phenyl ethanol.

3. The process according to claim 1, wherein step (a) is carried out in the gas phase at a temperature in the range of 230 to 320° C. using an alumina-based dehydration catalyst.

4. The process according to claim 1, wherein the base in step (c) is selected from one or more of sodium hydroxide, potassium hydroxide, sodium carbonate and potassium carbonate.

5. The process according to claim 1, wherein the treated stream of step (c) is separated in step (d) by settling, coalescing or centrifuging.

6. The process according to claim 1, wherein a portion of the styrene or substituted styrene-rich product stream from step (d) is recycled to step (b) of the process.

7. The process according to claim 1, wherein steam for use in step (e) is obtained from re-boiled bottom product of the stripping column or is injected into the stripping column from an external source.

8. The process according to claim 1, wherein the stripping column operates at atmospheric pressure, above atmospheric pressure or under vacuum.

9. The process according to claim 1, wherein some or all of the treated stream comprising steam and styrene or substituted styrene from step (e) is recycled to step (d).

* * * * *